United States Patent [19]
Leitao

[11] Patent Number: 6,069,295
[45] Date of Patent: *May 30, 2000

[54] IMPLANT MATERIAL

[75] Inventor: Eugenia Ribeiro de Sousa Fidalgo Leitao, Tytherington, United Kingdom

[73] Assignee: IsoTis B.V., Bilthoven, Netherlands

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/855,835

[22] Filed: May 12, 1997

[30] Foreign Application Priority Data

May 10, 1996 [EP] European Pat. Off. .............. 96201293

[51] Int. Cl.$^7$ ...................................................... A61F 2/02
[52] U.S. Cl. ............................. 623/11; 623/16; 433/201.1
[58] Field of Search ................................ 623/10, 11, 16, 623/18, 20, 21, 22, 23; 606/76; 427/2.26, 2.27; 433/199.1, 200.1, 201.1

[56] References Cited

U.S. PATENT DOCUMENTS

| | | | |
|---|---|---|---|
| 3,984,914 | 10/1976 | Schwartz | 32/10 |
| 4,145,764 | 3/1979 | Suzuki et al. | 3/1.9 |
| 4,330,891 | 5/1982 | Brånemark et al. | 3/1 |
| 4,538,306 | 9/1985 | Dorre et al. | 623/20 |
| 4,636,526 | 1/1987 | Dorman et al. | 521/61 |
| 4,687,487 | 8/1987 | Hintermann | 623/18 |
| 4,746,532 | 5/1988 | Suzuki et al. | 427/2 |
| 4,818,559 | 4/1989 | Hama et al. | 427/2 |
| 4,846,837 | 7/1989 | Kurze et al. | 623/16 |
| 4,847,163 | 7/1989 | Shimamune et al. | 428/469 |
| 4,863,474 | 9/1989 | Brown et al. | 623/16 |
| 4,879,136 | 11/1989 | Pölz | 427/2 |
| 4,880,610 | 11/1989 | Constantz | 423/305 |
| 4,911,953 | 3/1990 | Hosonuma et al. | 427/224 |
| 5,030,474 | 7/1991 | Saita et al. | 427/2 |
| 5,071,434 | 12/1991 | Tsuzuki et al. | 623/16 |
| 5,071,436 | 12/1991 | Huc et al. | 623/16 |
| 5,128,169 | 7/1992 | Saita et al. | 427/2 |
| 5,141,576 | 8/1992 | Shimamune et al. | 427/2 |
| 5,180,426 | 1/1993 | Sumita | 106/35 |
| 5,205,921 | 4/1993 | Shirkanzadeh | 623/16 |
| 5,219,361 | 6/1993 | von Recum et al. | 623/11 |
| 5,344,457 | 9/1994 | Pilliar . | |
| 5,358,529 | 10/1994 | Davidson | 623/20 |
| 5,456,723 | 10/1995 | Steinemann et al. | 623/16 |
| 5,478,237 | 12/1995 | Ishizawa | 433/173 |
| 5,484,286 | 1/1996 | Hansson | 433/201.1 |
| 5,603,338 | 2/1997 | Beaty | 623/16 |
| 5,730,598 | 3/1998 | Story et al. | 433/201.1 |
| 5,766,669 | 6/1998 | Pugh et al. | 427/2.27 |
| 5,947,893 | 9/1999 | Agrawal | 623/16 |

FOREIGN PATENT DOCUMENTS

| | | |
|---|---|---|
| 450939 | 10/1991 | European Pat. Off. . |
| 2045083 | 10/1980 | United Kingdom ..... 623/16 |
| 95/13101 | 5/1995 | WIPO ..... 623/16 |
| WO 95/13102 | 5/1995 | WIPO . |
| WO 96/39202 | 12/1996 | WIPO . |

*Primary Examiner*—Paul B. Prebilic
*Attorney, Agent, or Firm*—Banner & Witcoff, Ltd.

[57] ABSTRACT

The invention provides a nanotechnology process for implant surface treatment for producing an implant article. The nanotechnology process comprises subjecting a nonporous material to a mechanical or chemical surface treatment until a surface roughness with an average peak distance (Ra value) between 10 and 1,000 nm is obtained. The roughened surface can subsequently be subjected to precipitation of calcium phosphate from a solution containing calcium and phosphate ions.

11 Claims, 13 Drawing Sheets

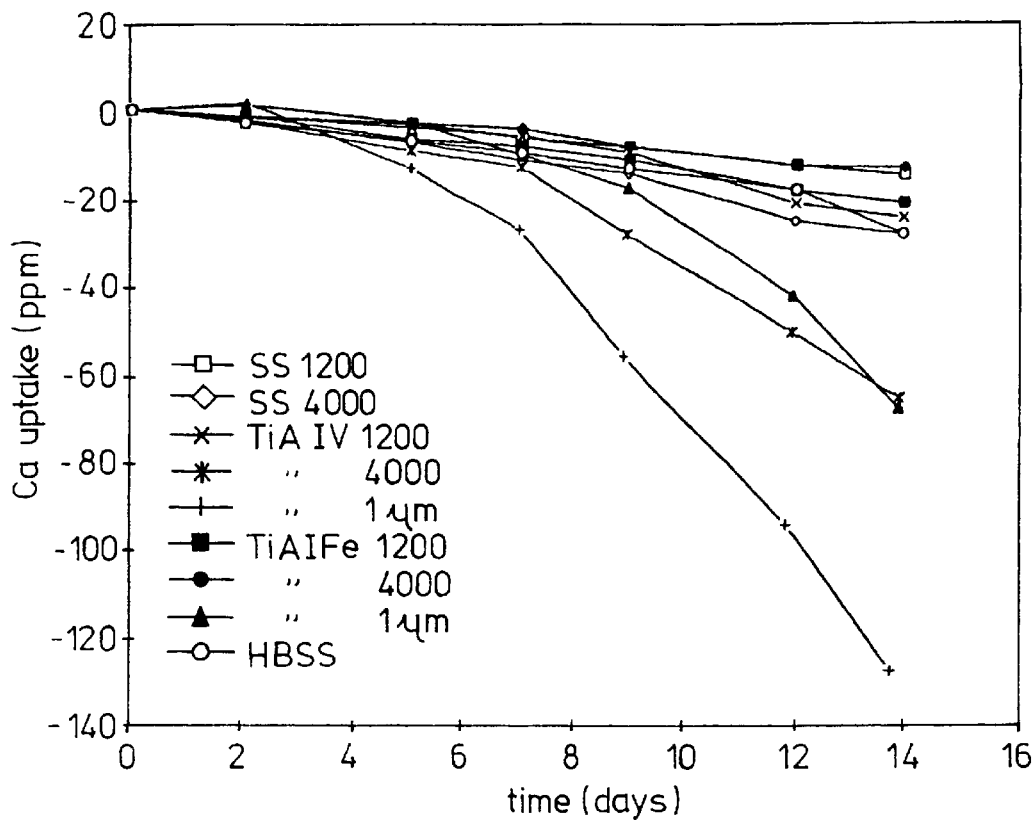
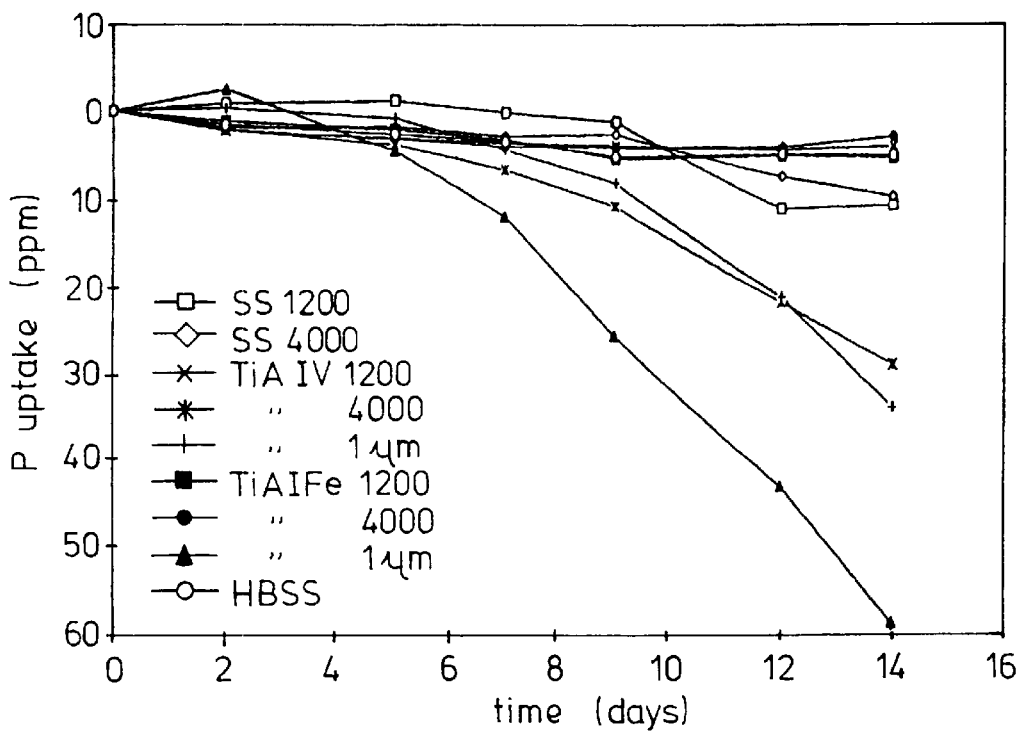

IMPLANT MATERIAL

BACKGROUND OF THE INVENTION

The present invention relates to an implantable device, to a process of producing such a device and to the biomedical use of such a device.

U.S. Pat. No. 5,456,723 discloses an implant having a porous metallic surface which has been treated by sandblasting and reductive acid etching resulting in a surface microroughness having a maximum peak-to-valley height of about 20 to 30 μm and a roughness spacing of from 0.5 to 10 μm, preferably of about 1–5 μm. The extremely sharp, comb-like structure is necessary in order to achieve sufficient adhesion between the implant and the coating material (hydroxyapatite) formed on it by anchoring the hydroxyapatite in the implant.

A drawback of most hydroxyapatite-coated implants is that the anchoring of hydroxyapatite onto the implant requires high processing temperatures, which limit the choice of substrate materials and result in higher processing costs. The previously preferred technique for coating implant materials with hydroxyapatite is plasma deposition (for a review, see P. Screkian, in *Hydroxylapatite Coatings in Orthopaedic Surgery*, Ed Geesink and Manley, Raven Press NY, 1993, p. 81–87). Another disadvantage of the plasma deposition technique, in addition to the high temperatures involved, resides in the relatively large particle size, in the order of 30–70 μm.

An aim of the present invention is to provide an implantable device that can be used in a wide variety of biomedical applications (surgery, bone-replacement, prosthodontics etc.), and results in an effective bone formation and can be processed at ambient temperatures.

SUMMARY OF THE INVENTION

The aim is achieved by a shaped article suitable as an implant of a solid, i.e. non-fluid, porous or non-porous material having a surface nanoroughness with an average peak distance (Ra value) between 10 nm and 1,000 nm, giving rise to the formation of a composite coating when placed in solutions of bone-forming components.

The surface roughness is a critical factor of the article according to the invention. The surface roughness is defined herein by the average peak distance, i.e the average spacing between protrusions on the surface (Ra value). This average peak distance can be determined e.g. by means of Scanning Electron Microscopy (SEM). In general, the average peak distance should be 1,000 nm or less. The most suitable roughness depends on the nature of the material of the article. For articles made of titanium, the average peak distance can be e.g. from 10 to 200 nm, for polymeric material, the preferred peak distance is from 20 to 500 nm, whereas for stainless steel the peak distance is advantageously between 50 and 1,000 nm. In general, the preferred average peak distance range is between 2 and 500 nm.

The depth of the surface roughness of the article is less critical than the peak distance. However, a minimum depth is desirable, in particular a peak height—with respect to the deepest sites on the surface—of at least 20 nm, up to about 2,000 nm. The preferred average depth is of the same order of magnitude as the average peak distance, and is in particular from 50 nm to 1,000 nm. The average depth can also be determined by means of Scanning Electron Microscopy.

The substrate of the implant article can be of various materials. These include metals, in particular biocompatible metals such as titanium, tantalum, niobium, zirconium and alloys thereof, as well as stainless steel. Another useful class of bio-compatible materials comprises organic natural and synthetic polymers such as polyethylene, polypropylene, polytetrafluoroethylene (Teflon®), which may also be bio-degradable polymers such as polyglycolic acid, polylactic acid or certain polysaccharides. Ceramic materials such as calcium phosphate, alumina or bioglass, as well as composite materials, can also be used as an implant substrate. The material may be porous or non-porous. Where it is porous, the pores are distinguished from the valleys of the surface roughness by their depth: i.e. the pores have depths substantially greater than 2 μm, and the surface roughness may be superimposed on the pore walls.

The substrate having the surface roughness as defined above can very efficiently be coated with a layer of a calcium phosphate, either in vitro, or in vivo. If the calcium phosphate coating is applied in vitro, the calcium phosphate layer can be relatively thin, on the order of from e.g. 50 nm to 200 μm, especially from 1 to 50 μm. The calcium phosphate preferably forms small crystals, producing an amorphous-like structure. The calcium phosphate can be any combination of calcium and phosphate ions, optionally together with e.g. hydroxide, chloride, sulphate, nitrate etc. anions or hydrogen, sodium, potassium, magnesium etc. cations. Preferably, the calcium phosphate is not a hydroxy-apatite, since the latter tends to have too large particles.

The calcium coating can be applied from a solution containing calcium and phosphate ions. The solution may be saturated ox even super-saturated, but it may also be relatively diluted. This is an important advantage of the present invention since it allows the formation of a calcium phosphate coating from practically any solution containing calcium and phosphate ions. The pH range of the calcium phosphate containing solution may be between 4 and 10, preferentially between 6 and 8.

The invention also provides a process of producing a shaped article as described above, comprising subjecting a solid material to a mechanical or chemical surface treatment until a surface roughness with the required average peak distance (Ra value) is obtained.

The mechanical surface treatment may e.g. be a sanding or scoring treatment using conventional sandpaper, emery paper or glass paper having an appropriate fineness, e.g. grade 4000, optionally in the presence of water or other fluids. Diamond paste can also be used in the mechanical surface treatment. The surface roughening can further be obtained by powder blasting, using suitable fine powders. The chemical surface treatment may e.g. be a treatment with a strong, preferably mineral, acid solution, such as hydrofluoric, hydrochloric, sulphuric, nitric, perchloric acid or combinations thereof, optionally followed by oxidising agents such as nitric acid, peracids, hydroperoxides or hydrogen peroxide, optionally followed by neutralising steps. It is important that the surface roughening is performed under controlled conditions to ensure a uniform result.

The surface-roughened implantable devices according to the invention are intended for biomedical use, i.e. as a bone substitute, a joint prosthesis, a dental implant (prosthodontics), a maxillofacial implant, a vertebral surgery aid, a transcutaneous device (stoma and the like) and other medical or cosmetic devices. Such implants can serve as a bone replacement or bone reinforcement, but also as a means of fixing a device to a particular bone.

The implantable devices can be provided as such, i.e. without calcium phosphate coating. Bone formation can then be induced in vivo due to the presence of the specific surface roughening, which can result in the formation of a calcium phosphate coating in situ. The articles can also be pre-coated with calcium phosphate, the precoat serving then to accelerate and enhance bone formation and fixation of the implant in the target organism.

BRIEF DESCRIPTION OF THE DRAWINGS

Some illustrative embodiments of the invention, and the best mode contemplated of carrying out the invention, are described in detail below with reference to the accompanying drawings in which:

FIG. 1—Ca concentration as a function of time

FIG. 2—P concentration as a function of time

FIG. 3—SEM photomicrographs of the metal surfaces after immersion in HBSS.

DETAILED DESCRIPTION OF THE PREFERRED EMBODIMENTS

EXAMPLE 1

Materials and Methods

Figure 3A:
FIG. 3A: Ti-6Al-4V 1200.
Figure 3B:
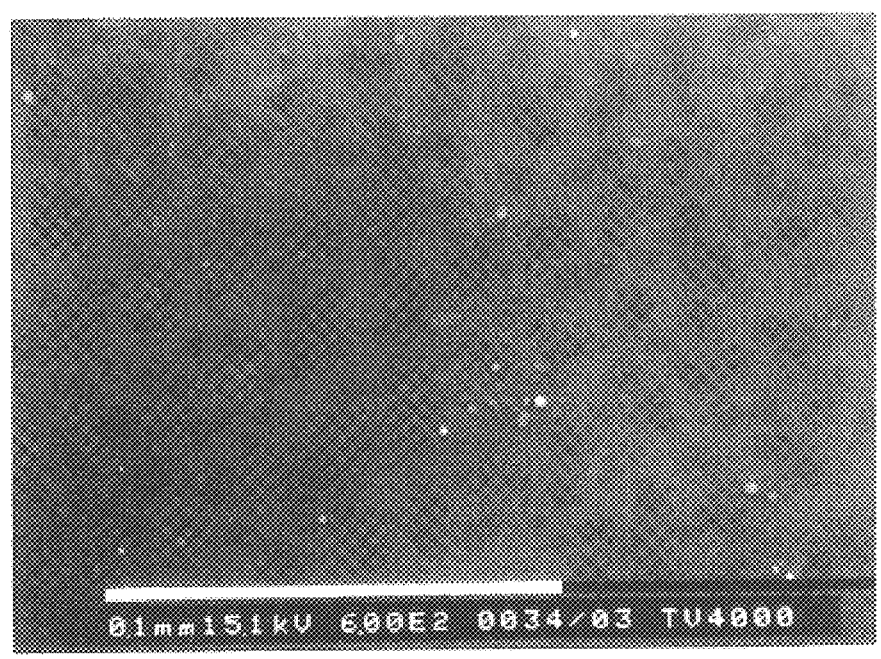
FIG. 3B: Ti-6Al-4V 4000.
Figure 3C:
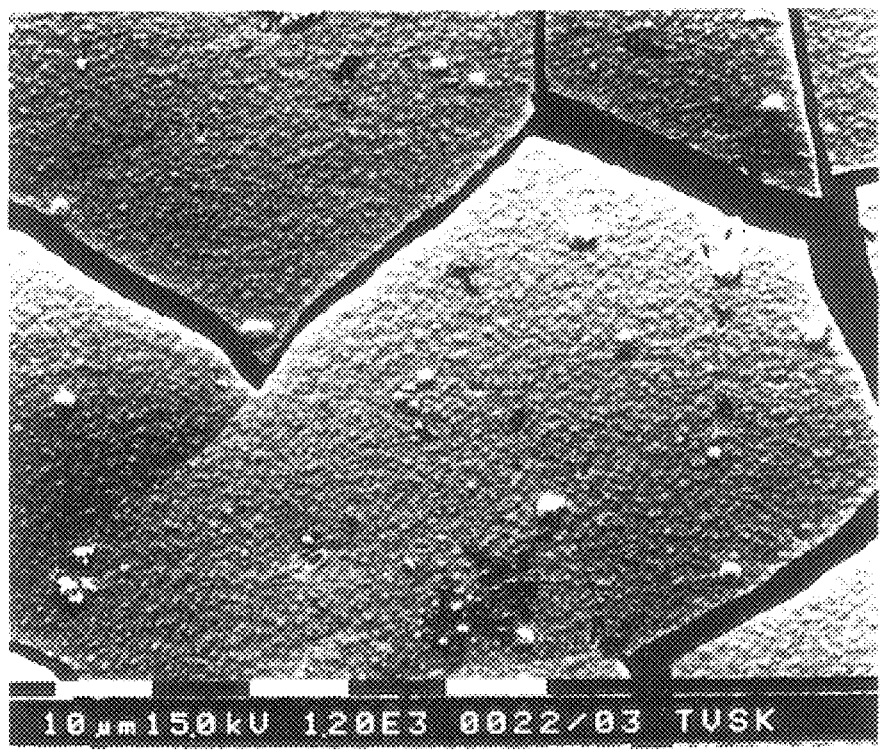
FIG. 3C: Ti-6Al-4V 1 μm.
Figure 3D:
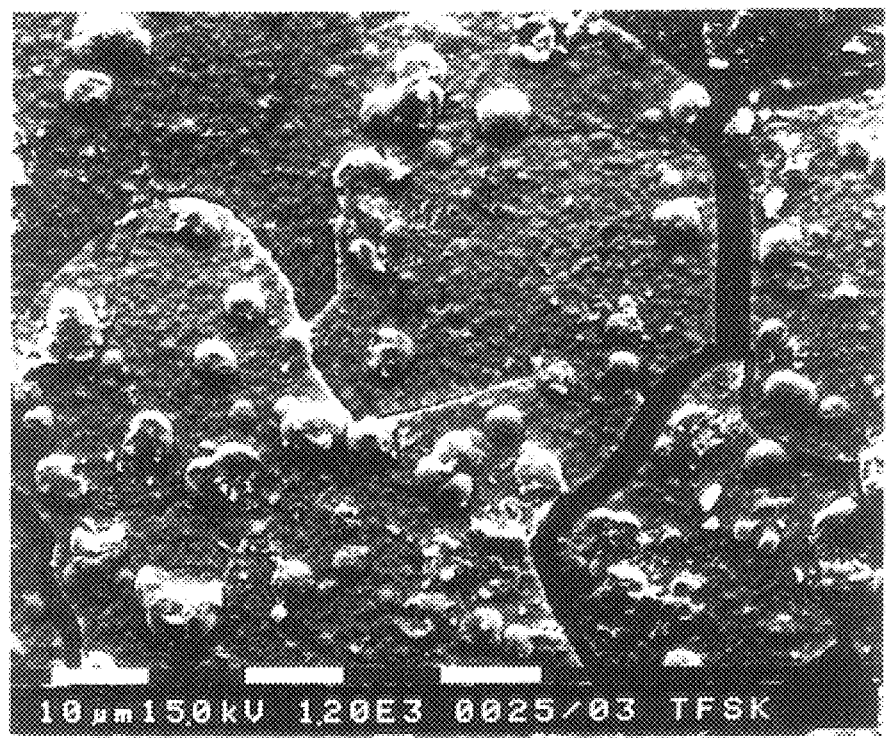
FIG. 3D: Ti-Al-2.5Fe 1 μm.
Figure 3E:
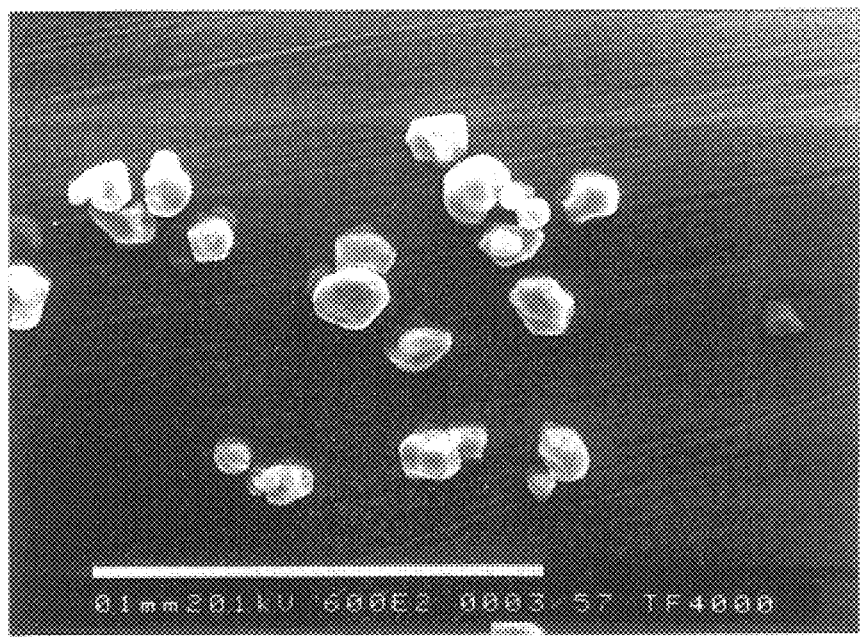
FIG. 3E: Ti-Al-2.5Fe 4000.
Figure 3F:
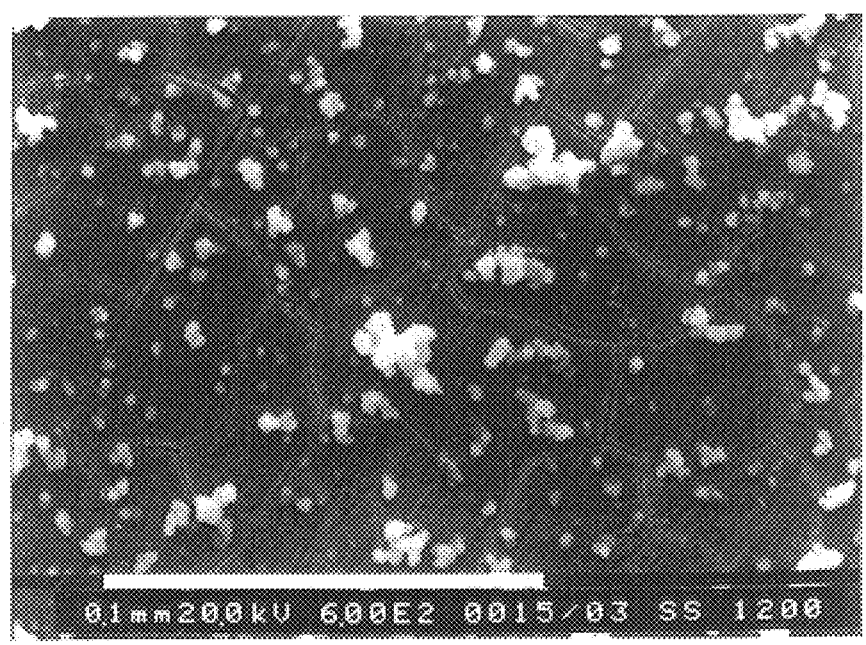
FIG. 3F—stainless steel 1200

Ti-6Al-4V and Ti-Al-2.5Fe samples, 9.15 mm and 5 mm in diameter respectively and 1.5 mm thick, were used. They were ground flat in SiC papers, 1200, 4000 grit and diamond polished down to 1 μm. 316L stainless steel samples, ca. 80 mm$^2$, were also ground in SiC papers, 1200 and 4000 grit. All samples were ultrasonically cleaned in 90% ethanol for 20 minutes followed by a 20-minute double rinse with distilled water and dried under a flow of hot air. The surface roughnesses were measured with a laser profilometer (Perkin Elmer). Table 1 shows the results of the following roughness parameters: $R_a$—arithmetic mean of the roughness height, $R_z$—mean peak-to-valley height and $R_{max}$—maximum roughness depth.

After surface polishing and cleaning, all samples were immersed in Hanks' Balanced Salt Solution (HBSS) at 37° C. for 14 days in separate polyethlene containers. To allow a constant supply of solution this was changed every 48 hours. Empty polyethylene containers were used as reference. A sample of each retrieved solution was stored in a 2 mL Eppendorf™ at 4° C. Ca and P concentrations in these solutions were later determined by atomic absorption spectrometry (Varian SpectAA 300) and spectrophotometry (Vitalab 21, Vitalab Scientific), respectively. All the results are the average of at least three measurements.

All surfaces were observed by scanning electron microscopy (Philips SEM 525M) before and after immersion and analysed by XRMA (Voyager XRMA, NORAN Instruments). XRD (Philips Thin-film XRD) was used to determine the structure of the precipitate layer, and AFM was used to observe its morphology on polished titanium alloys.

Results and discussion

FIG. 1 shows the Ca concentrations as a function of time, A monotonic decrease of the Ca concentrations was detected in the solutions that were in contact with the alloys. The same phenomenon was observed for the reference HBSS. Until day 5 all curves were similar but after day 5 the Ti-6Al-4V 1 μm samples exhibited a higher decrease, which reaches 123±1.5 ppm. For both Ti-6Al-4V 4000 and Ti-Al-2.5Fe 1 μm samples the Ca concentration decreased more rapidly after day 7 attaining similar final Ca uptake concentrations, 61±2.3 and 63±1.5 ppm, respectively. All other surfaces exhibited Ca uptake values between 5 and 20 ppm.

FIG. 2 shows the P concentration as a function of time. The P uptake curves, like the Ca determinations, also showed a decrease as a function of time. The Ti-6Al-4V 4000 and 1 μm and the Ti-Al-2.5Fe 1 μm showed the highest P uptake; 29±2.1, 34±1.5 and 58.5±2.2 ppm, respectively. These findings suggest that a Ca and P rich precipitate is formed on all the surfaces from HBSS. In fact, a white film deposited on the polyethylene that contacted the HBSS could be seen. Ti-Al-2.5Fe 4000 and 1200 showed the lowest Ca and P uptake. The decrease in both Ca and P was attributed to the growth of precipitate nuclei on the surfaces from the HBSS solution. Similar behaviour was found by Li et al. [6] after immersion of silica-gel and gel-derived titania in a Simulated Body Fluid; Radin et al. [2] also reported a decrease in Ca and P concentration in Simulated Physiological Solution after the immersion of ceramic particles.

FIG. 3 shows SEM photomicrographs of the metal surfaces after immersion in HBSS. Comparing the photographs on FIG. 3 it can be seen that the precipitate layer has a plate morphology on which "globules" and/or crystals grow. XRMA revealed a higher quantity of Ca and P on these particles than in the plate precipitate. It was possible to observe that the plates fractured on some of the surfaces, namely Ti-6Al-4V 1200 and 1 μm, Ti-Al-2.5Fe 1 μm and stainless steel 1200. The orientation of the fractures does not seem to depend on the orientation of the grinding flaws as it is possible to observe a random cracking of the plates. The precipitate formed on Ti-6Al-4V 4000 shows a continuous texture at the same magnification as the other observations. It was only possible to detect fractures on these surfaces, on the Ca and P rich layer, at magnifications higher than 2400×.

Li et al. [6] performed a series of experiments in which silica-gel was immersed in SBF. They suggest that the regulation of apatite growth is related to the Ca/P molar ratio of the fluids. Fugishiro et al. [1] obtained different HA morphologies by immersing Fe and Ti in Ca(EDTA) $NaH_2PO_4$ solution. Various concentrations of Ca(EDTA) had a direct effect on the morphology of the hydroxyapatite film.

The SEM observations suggest that the morphology of the precipitate layer seems to be dependent both on material and surface finishing as the immersion fluid was the same in all experiments.

Figure 4:
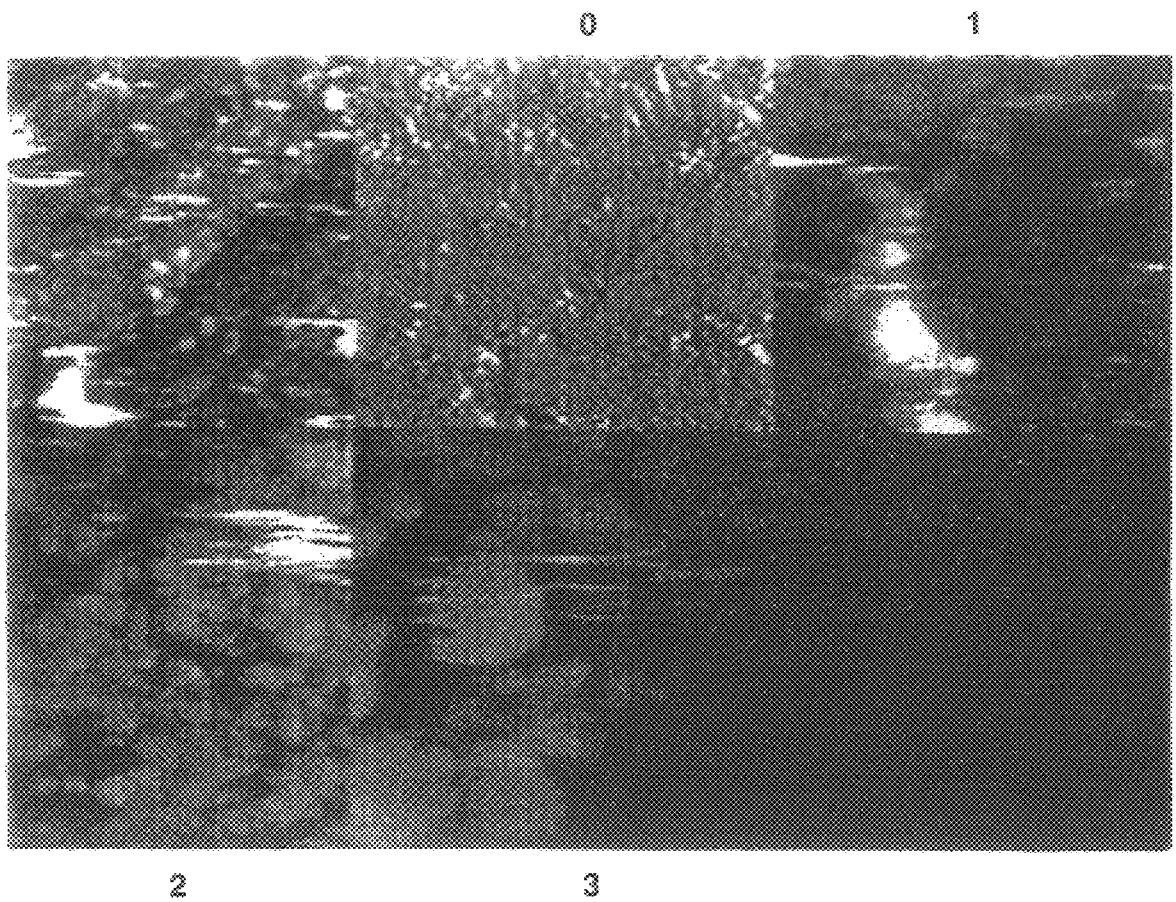
FIG. 4—AFM photomicrograph of a Ti-Al-2.5Fe 1 μm sample after immersion in HBSS. Increasing magnification from field 0 to 3. Scanning length from field 3: 1.5 μm.

FIG. 4 shows an AFM photomicrograph from a Ti-Al-2.5Fe 1 μm sample. It is apparent that the calcium phosphate rich coating is constituted by the agglomeration of spherical particles. Similar results were obtained for the Ti-6Al-4V 1 μm surfaces. It seems that the formation of the coating starts with heterogeneous precipitation of nuclei which gather with time until all the surface is covered.

It was noticeable that the Ti-Al-2.5Fe alloy surfaces 4000 and 1200 did not exhibit plate precipitates. It was only possible to observe small scattered deposits which had a similar morphology to crystals. XRMA acquisition on the flat-ground surfaces showed the presence of no Ca or P. The same acquisition on the crystals showed the presence of the alloy elements, Ca and P, associated with Si. Si seems to act as a nucleus for the precipitation and growth of the crystals. This impurity is probably due to the SiC emery paper used during the surface preparation. Either the degreasing and cleaning of the surface was not sufficient, on these surfaces, to remove the SiC or some SiC particles might be anchored in the alloy's surface as Ti-Al-2.5Fe is a softer material than the other alloys.

Figure 5:
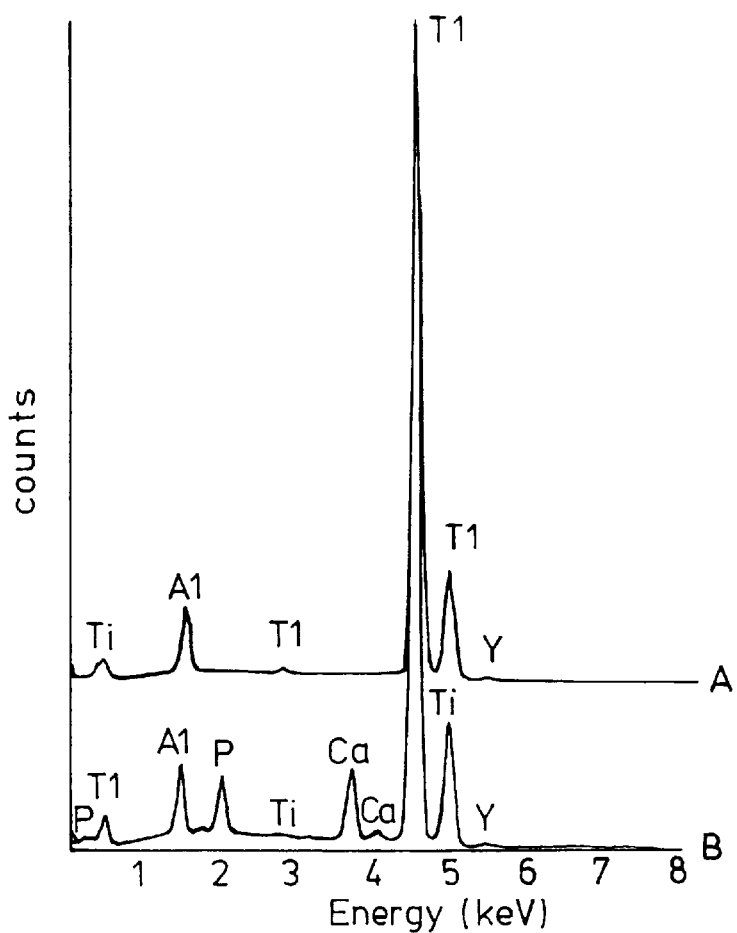
FIG. 5—XRMA spectra acquired on a Ti-6Al-4V 4000 sample before (A) and after immersion (B) in HBSS.

FIG. 5 exhibits XRMA spectra acquired in a Ti-6Al-4V 4000 sample before and after immersion in HBSS. One can observe the presence of the alloy elements as well as very well defined Ca and P peaks on the after-immersion spectra. The calculated Ca/P ratio is 1.56±0.03 which indicates that the precipitate probably consists mainly of tricalcium phosphate.

Figure 6:
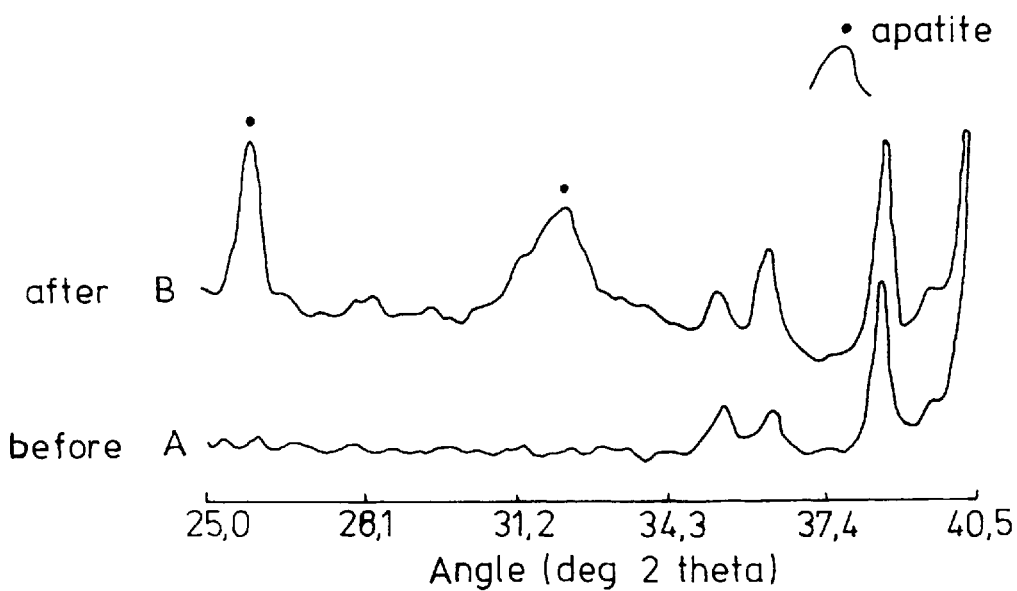
FIG. 6—XRD spectra acquired on a non-immersed (A) and immersed (B) Ti-6Al-4V 1 μm surface FIG. 7. Surface chemical composition (in atomic percent) of the "as received" coating.

FIG. 6 shows XRD spectra acquired on non-immersed (A) and immersed (B) Ti-6Al-4V 1 μm surfaces. On the immersed samples one can observe the appearance of a well defined [002] peak and a broader peak which seems to be constituted by the junction of peaks [211] and [112] indicating the amorphous characteristics of the calcium phosphate. These results suggest that the precipitate layer has an amorphous apatite-like structure. Similar results were obtained for the Ti-Al-2.5Fe 1 μm samples. The thickness of this layer was previously determined by, SEM observations and is ca. 5 μm. Li et al. [6] monitored the development of hydroxyapatite deposits on gel-derived titania, as a function of time, after immersion in Simulated Body Fluid. In the initial stages they detected scattered precipitates all over the surface which increased in number and size until, eventually, all the surface was covered by a 10 μm coating. Ducheyne et al. [5] reported the formation of small deposits on titanium discs after 1-day exposure to a Simulated Physiological Solution. Two weeks of differential immersion were needed to produce an apatite layer with a thickness of 1 μm.

Hanawa et al. [3] also reported that apatite is naturally formed on titanium when titanium is immersed in a solution whose pH is similar to that of the bioliquid. They reported a thickness of 7 nm of the apatite film grown on Ti-6Al-4V which makes it impossible for this layer to exhibit any properties of calcium phosphate in this environment.

The present results indicate that a calcium phosphate with all apatite-like structure is naturally formed on the surfaces of polished titanium alloys. The thickness of this layer makes it a suitable surface for bone induction. Thicknesses of at least 1 μm are needed for the calcium phosphate to show its properties and cause bone induction [5].

Conclusions

The morphology of calcium phosphate precipitates depends on the metal substrate and its surface characteristics. It is possible to produce a naturally formed calcium phosphate coating by immersing metals such as titanium alloys and stainless steel in HBSS.

Ti-6Al-4V 4000 seems to be the surface that is most favourable to produce a continuous and more adherent apatite-like coating capable of bone induction.

EXAMPLE 2

Determination of calcium phosphate depth distribution on a titanium alloy substrate using x-ray photoelectron spectroscopy This example illustrates the determination of the depth distributions of selected elements in a calcium, phosphorous and oxygen-containing coating on a titanium alloy sample using depth profiling X-ray Photoelectron Spectroscopy (XPS or ESCA).

Materials

The samples were titanium alloy plates that had been surface treated according to the procedure of Example 1 to produce a calcium phosphate coating when immersed in calcification solutions or simulated body fluids. The samples were mounted directly to a standard XPS sample holder using a spring clip arrangement, with no pre-treatment. The outer coating surface was sufficiently electrically conducting that no electrostatic charging problems were encountered during X-ray irradiation or ion beam etching. All analyses were carried out using a Surface Science Instruments (SSI) M-probe operating at a base pressure of $3 \times 10^{-9}$ torr.

Methods

A survey spectrum was recorded from the "as received" surface, to determine the surface composition of the coating and therefore determine the elements to be monitored for the depth profile. The XPS depth profile was obtained by alternating argon ion sputtering (over an area of approx. 2×2 mm) and data acquisition (from an area of approx. 300 μm diameter centered in the etched crater). Elements analysed were carbon, oxygen, calcium, phosphorus, magnesium and titanium. Etch time per step was variable from 15 to 120 seconds per cycle and the etch rate was 3 nm/min using a total sputter time of 4470 seconds.

Results

Figure 7:
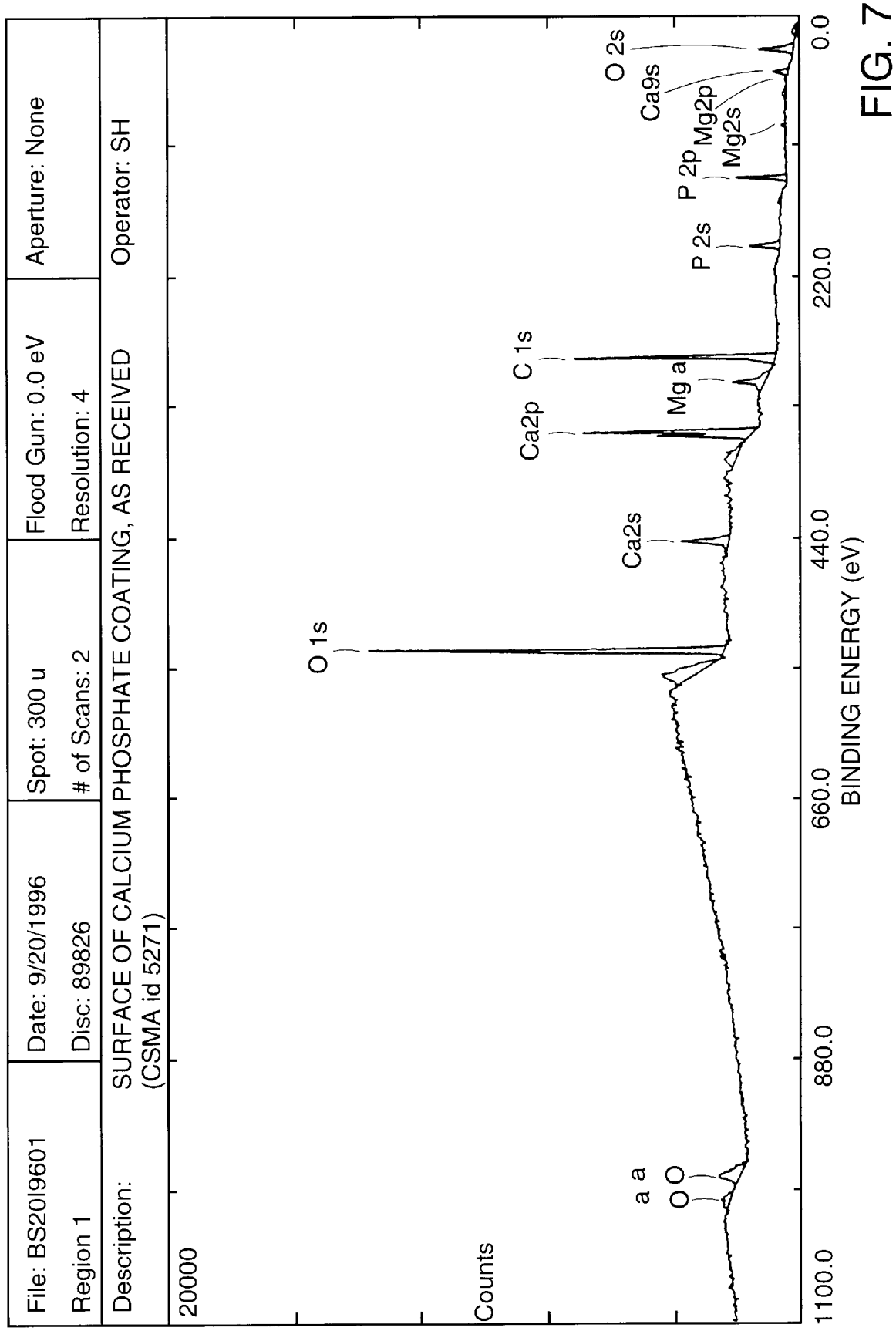
Figure 8:
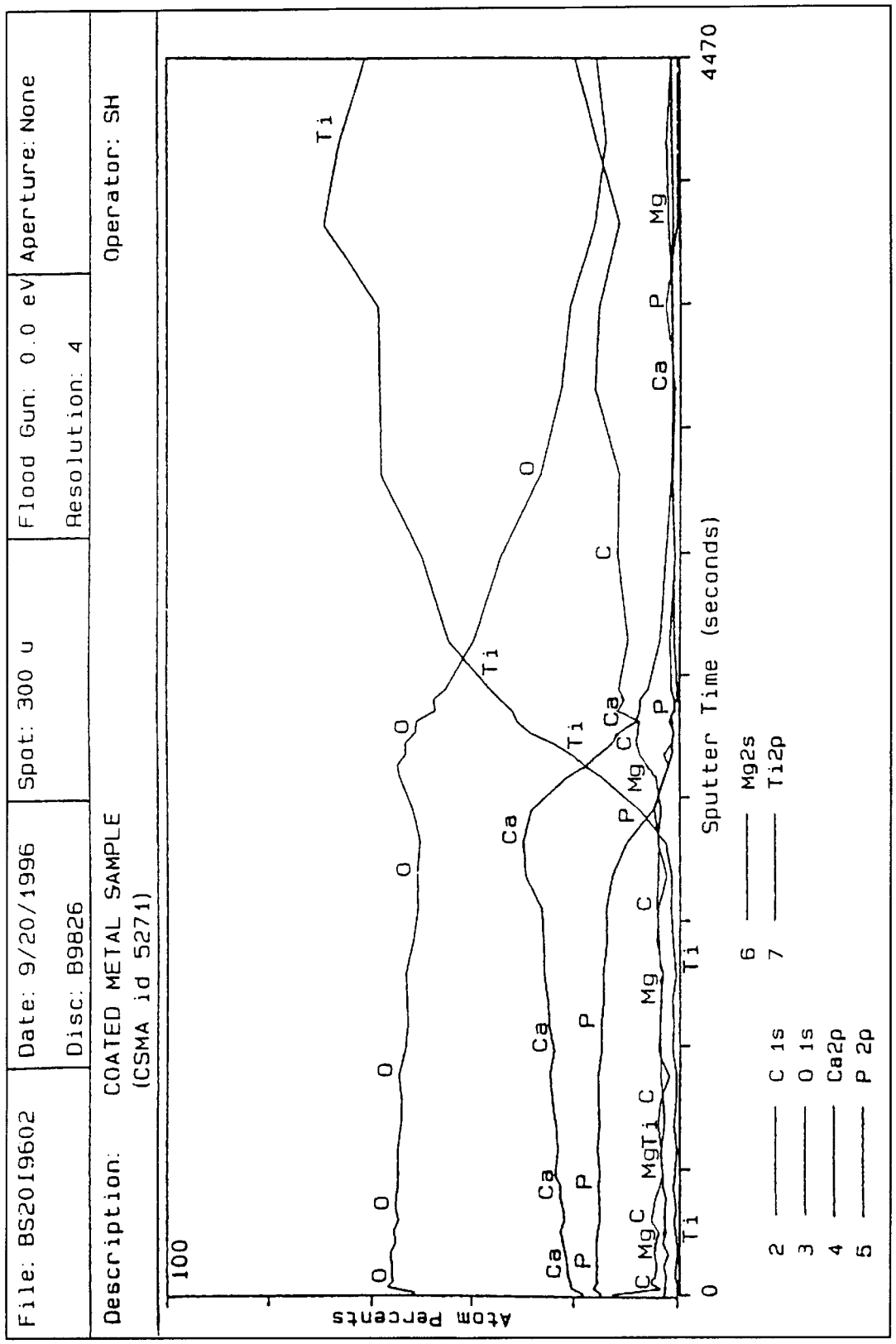
FIG. 8. Depth profile of the coating, from coating to substrate.

The surface chemical composition (in atomic percent) of the "as received" coating was: carbon 44.9%, oxygen 33.8%, calcium 10.5%, phosphorous 8.8%, magnesium 2.0% and titanium 0% (FIG. 7). The depth profile of the coating revealed a gradual transition of calcium and phosphorous from the coating to the substrate, indicating the incorporation of these elements in the surface (oxide layer), and thus a chemical bonding between coating and substrate (FIG. 8). The calcium-oxygen-phosphorous layer (calcium phosphate) is estimated as being approximately 90 nm, assuming a sputter rate of 3 nm per minute as calibrated on a tantalum pentoxide film on tantalum, and that the "interface" is defined as the point where the titanium reaches approx. 50% of its final value. A thin layer of titanium oxide separates the calcium phosphate layer from the titanium alloy substrate. The interface between the calcium phosphate and titanium shows changes in the oxygen, phosphorous, calcium and titanium chemistries. The XPS peak binding energies of calcium and phosphorous decrease at the interface with the titanium where a titanium oxide layer is found. An interphase region is likely to occur at the boundary and oxygen has been depleted from the calcium phosphate to form titanium dioxide at the interface. Metallic titanium is present below the interphase region. Magnesium is detected at 2–4 atomic percent throughout the calcium phosphate layer and increases slightly in concentration with depth towards the interface with the titanium (oxide). Carbon is found in the bulk of the titanium.

Conclusion

The calcium phosphate layer that is formed on the titanium alloy substrate is chemically bound to the substrate via its surface oxide layer.

EXAMPLE 3

Preparation of biomimetic calcium phosphate coatings on metallic implants

This example illustrates a new two-step chemical treatment for preparing an implant with a specific surface roughness, resulting in a metallic surface that allows fast precipitation of biomimetic calcium phosphate (Ca-P) coatings from in vitro super-saturated calcification solutions (SCS). The specific surface roughness results in the following advantages: (i) the biomimetic coatings directly induced from SCS are chemically bound to metallic substrates and show higher bone-bonding ability, (ii) the coatings can be produced onto complex-shaped and/or macro-porous implants, and (iii) it is a controllable and cost-effective way to acquire Ca-P coatings.

Materials and Methods

A newly developed two-step chemical treatment was performed on the metallic implant materials, i.e. commercially pure titanium (cp.Ti), annealed Ti6Al4V and porous tantalum (Ta), to produce a specific surface roughness. During this treatment, two series of chemical reagents were used for titanium (cp.Ti and Ti6Al4V) and tantalum implant materials, respectively, that resulted in the presence of the specific surface roughness necessary for the preparation of the coating. For the former, the samples were treated with a mixture of HCl and $H_2SO_4$, followed by immersion in a NaOH solution. The porous tantalum samples were treated with a mixture of HCl, $H_2SO_4$ and HF, followed by immersion in $H_2O_2$.

Two kinds of SCSs with different Ca and P concentrations, fast calcification solution (FCS) and commercial Hanks' balanced salt solution (HBSS). were used for preparing biomimetic Ca-P coatings. To promote the Ca-P nucleation on the metallic surfaces, a precalcification (Pre-Ca) procedure was performed on half the treated samples before immersion in the SCS. The Pre-Ca was carried out by incubating the samples in 0.5N $Na_2HPO_4$ overnight and then transferring them into saturated $Ca(OH)_2$ for 5 h. The FCS solution volume used for immersion was 15 ml per $cm^2$ of sample surface area. The samples were immersed in sealed polystyrene vials at 37° C. in a calibrated water-bath. Scanning electron microscopy (SEM) together with energy, disperse X-ray (EDX) analyses, X-ray diffraction (XRD) and infrared (IR) spectrophotometry were used to characterize the obtained Ca-P coatings.

Results

The biomimetic Ca-P coatings were fast precipitated on the treated cp.Ti and Ti6Al4V samples by immersion in both FCS and HBSS no matter whether the Pre-Ca procedure was performed or not. But the Pre-Ca treatments could dramatically speed-up the precipitation rate of the Ca-P coatings as listed in table 2.

Figure 9:
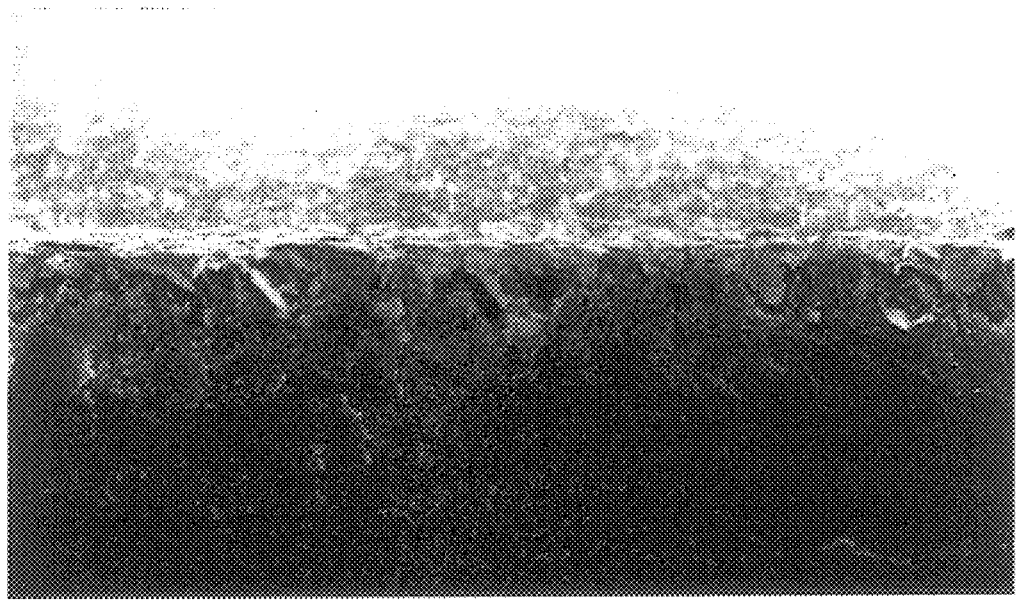
FIG. 9. Scanning electron micrograph of the Ca-P coating (CP) precipitated on cp.Ti (Ti) after 16 hours of immersion in FCS with Pre-Ca.
Figure 12:
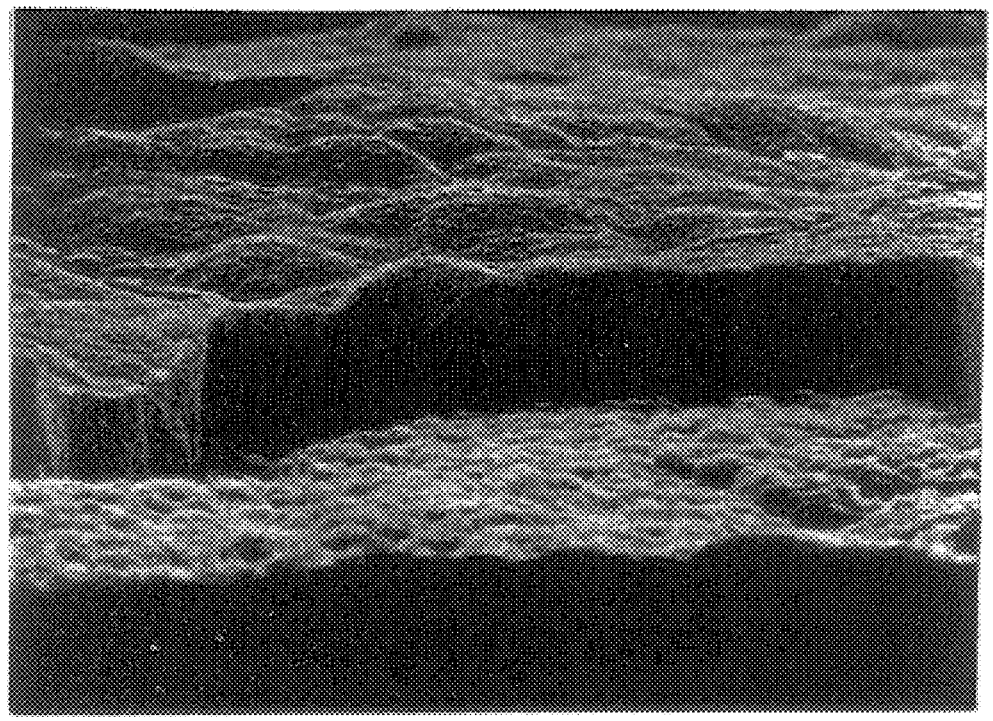
FIG. 12. Scanning electron micrograph of a dense Ca-P coating (CP) precipitated on cp.Ti from HBSS after 1 week of immersion with Pre-Ca.. The layer between coating and substrate is the titanium oxide layer (OL), formed as a result of the treatment.
Figure 10:
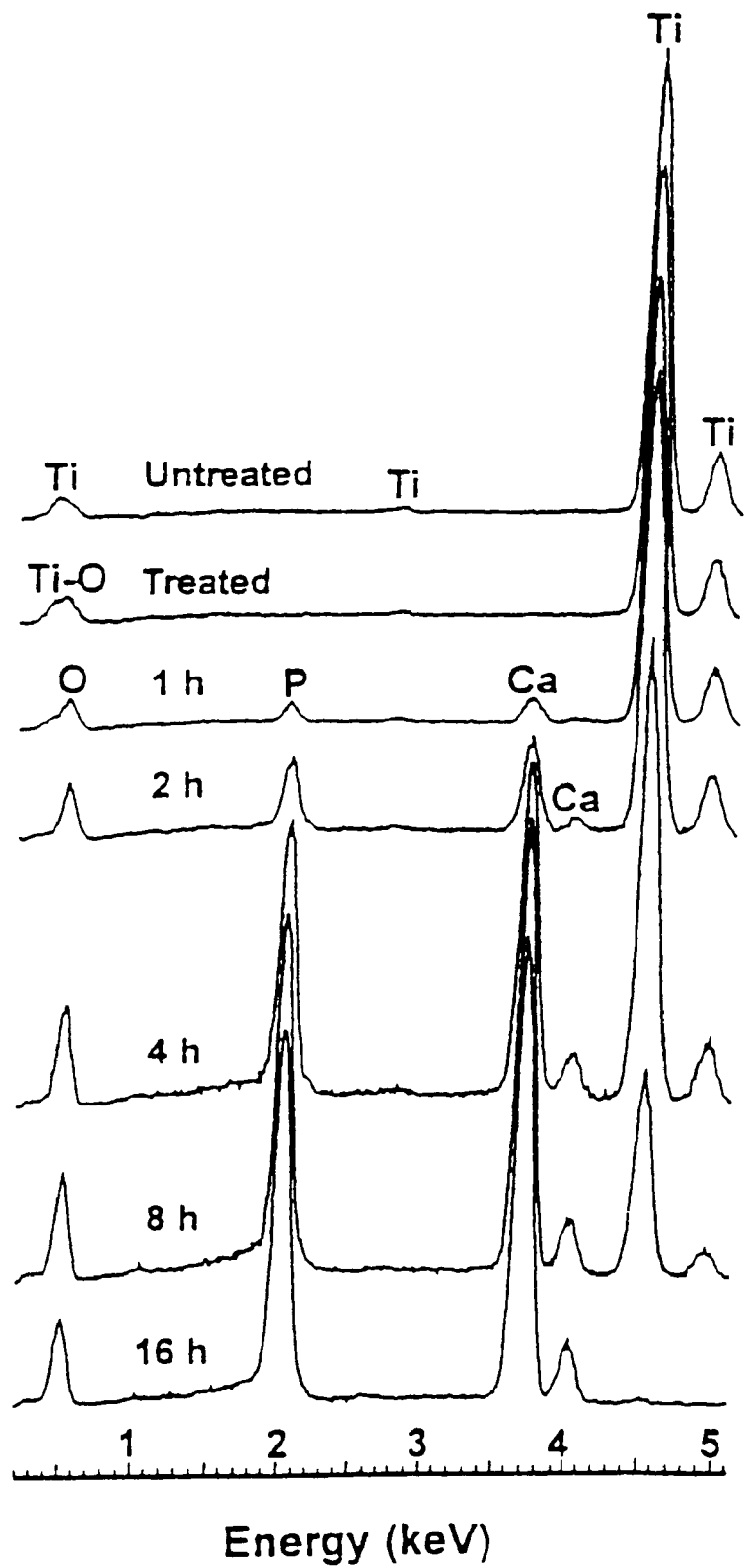
FIG. 10. EDX spectra of the cp.Ti surfaces non-treated, treated and immersed in FCS with Pre-Ca for different hours. The shoulder of 0 kα peak is clearly seen after the treatment. The Ca and P contents increased with the increase of immersion time.
Figure 11:
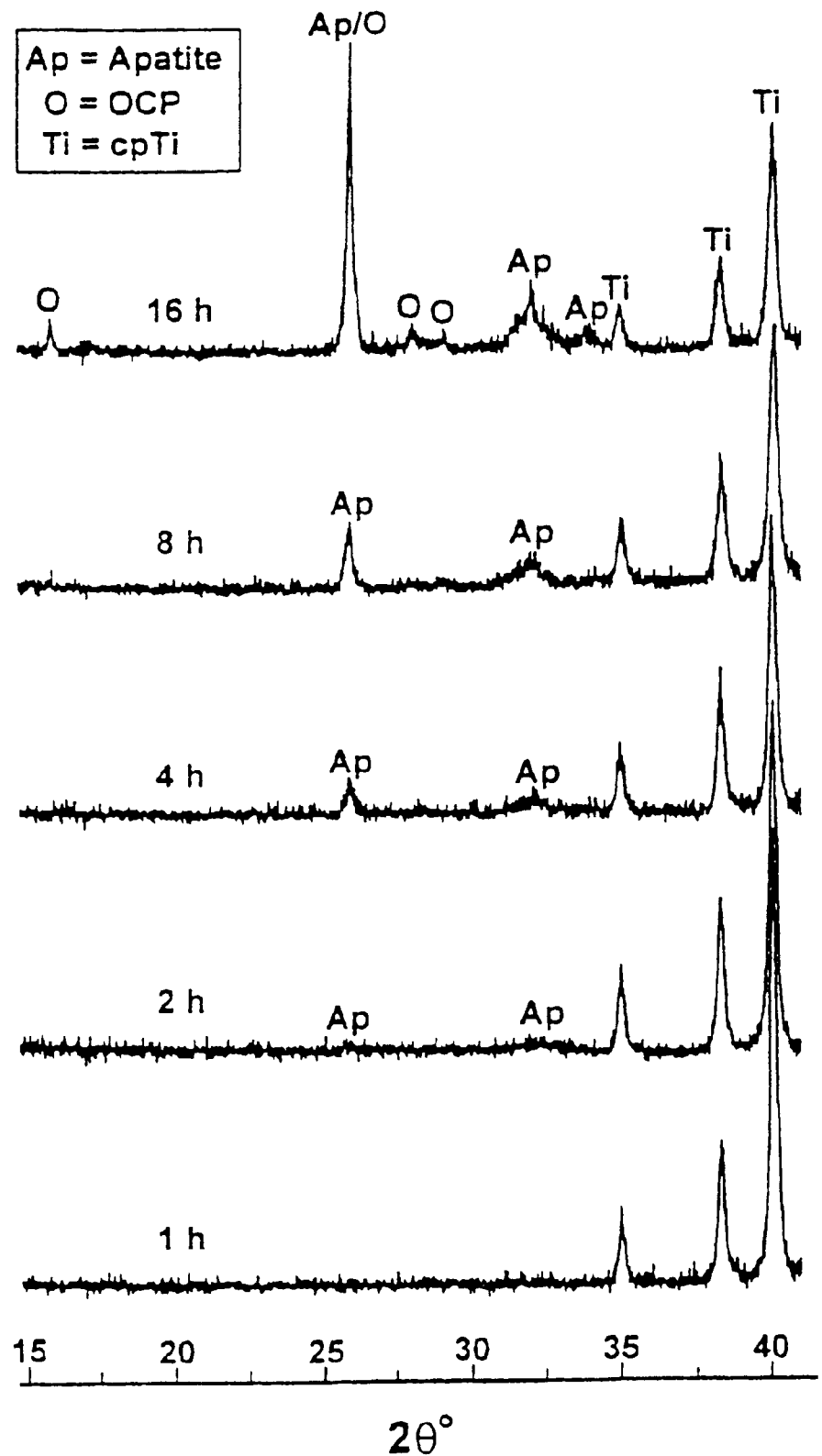
FIG. 11. XRD patterns of the cp.Ti surfaces after different hours of immersion in FCS with Pre-Ca. The counts of apatite peaks get higher with increased immersion times. Octa-calcium phosphate (OCP) starts to be formed at around 8 hours.
Figure 13:
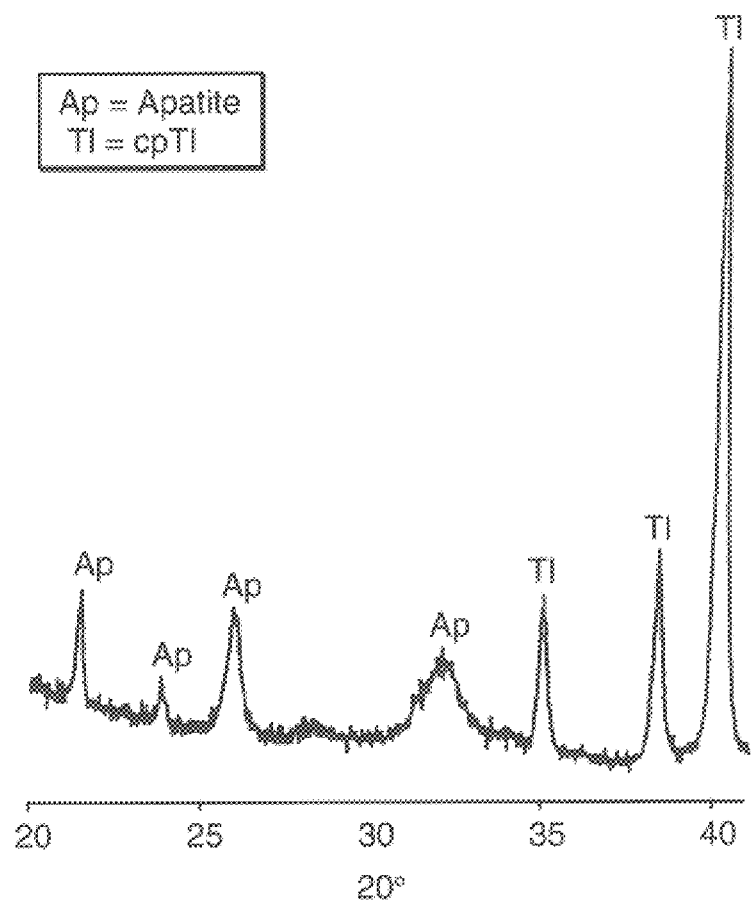
FIG. 13. Thin-film XRD pattern of a dense Ca-P coating deposited by immersion in HBSS with Pre-Ca for 1 week.
Figure 14:
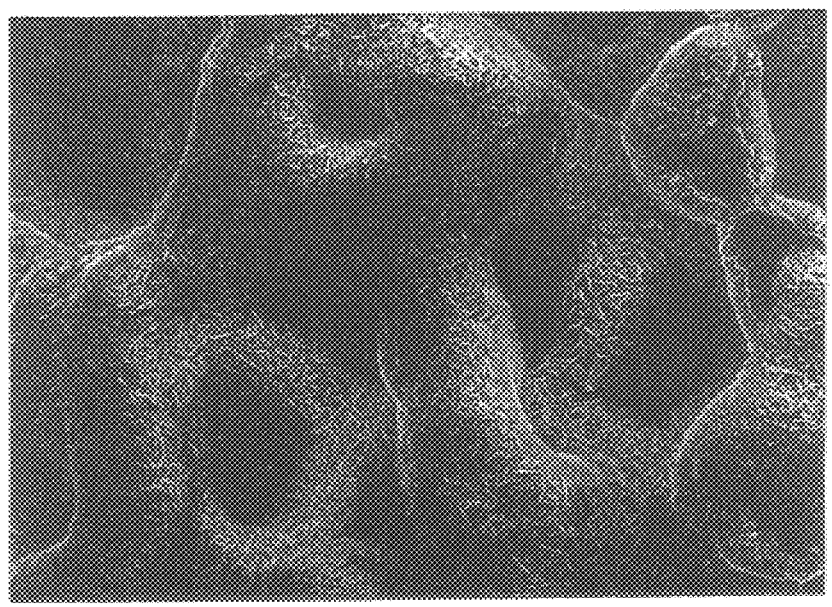
FIG. 14. Scanning electron micrograph of porous tantalum (Ta) after 2 days immersion in FCS with Pre-Ca. The coating is formed throughout the porous material.
Figure 15:
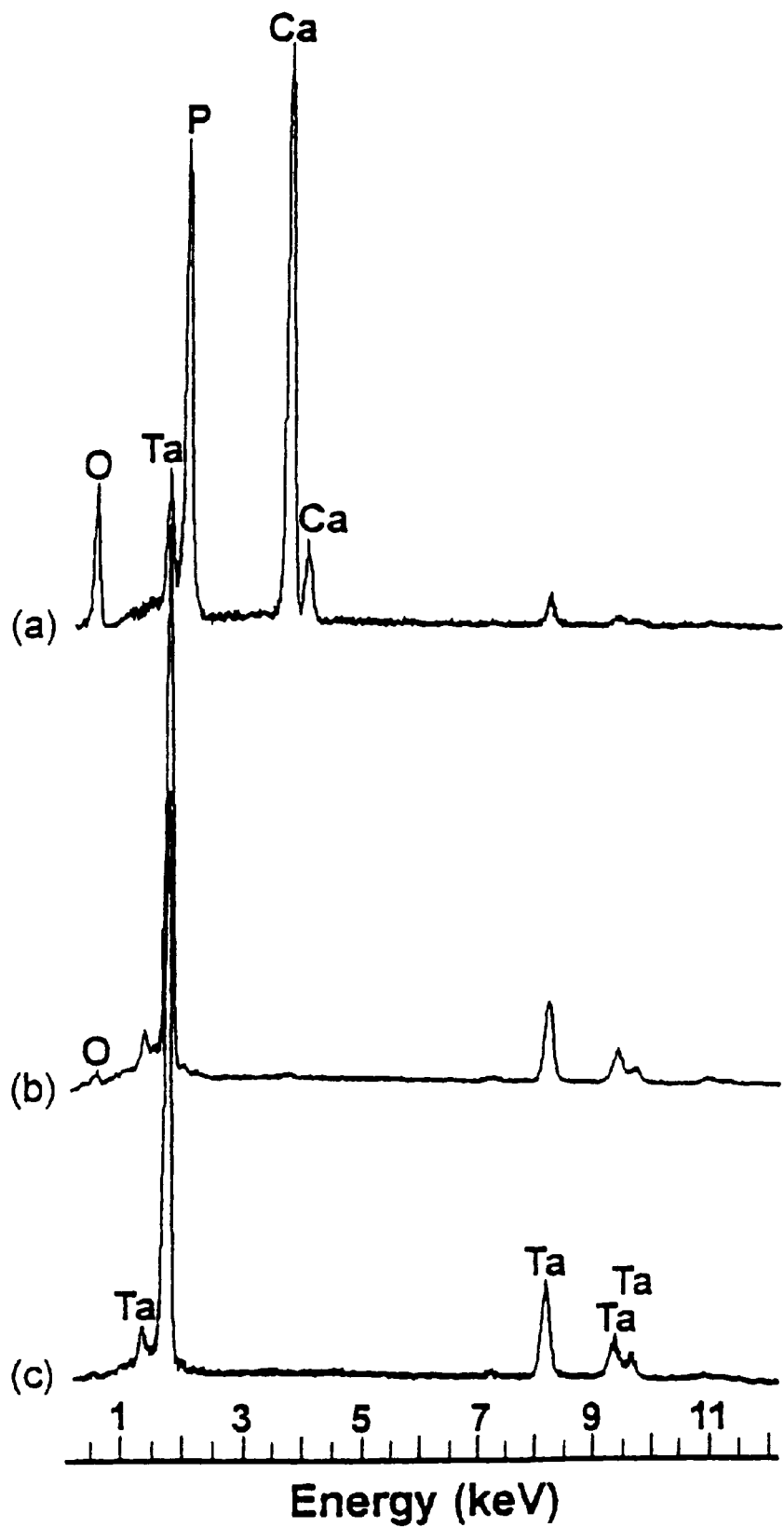
FIG. 15. EDX spectra of (a) non-treated, (b) treated, and (c) Pre-Ca treated, 2 day, FCS immersed porous tantalum (Ta) sample.

FIG. 9 shows that a biomimetic Ca-P coating, approximately 16 μm thick, was formed on treated cp.Ti after 16 hours of immersion in FCS with Pre-Ca. The coating got thicker with immersion time as indicated by EDX (FIG. 10) and XRD (FIG. 11) results. The precipitation rate of the Ca-P coating in HBSS is slower than that in FCS. But the coating from HBSS (FIG. 12) was much denser than that from FCS. The coating from HBSS mainly consisted of apatite (FIG. 13). Biomimetic Ca-P coatings could also be precipitated on porous Ta samples (FIG. 14) after the treatment. The surface content change of the sample was detected by EDX as shown in FIG. 15. It is noteworthy that no precipitation was observed on any untreated samples after 2 weeks of immersion in FCS or HBSS, even with Pre-Ca. The formation of a specific titanium and tantalum oxide layer after their treatments is probably the main reason for the inductive precipitation of Ca-P coatings by means of in vitro immersion in SCS. The procedure of the treatments for titanium implants and tantalum could not be exchanged, otherwise no CA-P coating was acquired.

Conclusions

This biomimetic calcium phosphate coating study has shown that:

The newly developed two-step treatment is an effective method to prepare bioactive metallic implant surfaces allowing fast precipitation of adherent biomimetic Ca-P coatings by in vitro immersion in SCS. The chemical reagents needed for the treatment of titanium implant materials and tantalum are different from each other.

The precipitation of Ca-P coatings could be dramatically accelerated by means of pre-calcifying the treated samples before the immersions.

The precipitation rate and composition of the Ca-P coatings can be adjusted by controlling the components of the SCSs (FCS or HBSS) for immersion.

TABLE 1

Surface roughness measurements results

| Surface finish | $R_a$ (μm) | $R_z$ (μm) | $R_{max}$ (μm) |
| --- | --- | --- | --- |
| Ti-6Al-4V 1200 grit | 0.47 ± 0.01 | 3.74 ± 0.04 | 5.13 ± 0.08 |
| Ti-6Al-4V 4000 grit | 0.24 ± 0.03 | 1.91 ± 0.31 | 2.46 ± 0.54 |
| Ti-6Al-4V 1 μm | 0.03 ± 0.00 | 0.35 ± 0.05 | 0.48 ± 0.03 |
| Ti—Al-2.5Fe 1200 grit | 0.42 ± 0.03 | 2.97 ± 0.35 | 3.47 ± 0.48 |
| Ti—Al-2.5Fe 4000 grit | 0.23 ± 0.01 | 1.97 ± 0.18 | 2.46 ± 0.34 |
| Ti—Al-2.5Fe 1 μm | 0.04 ± 0.01 | 0.28 ± 0.11 | 0.36 ± 0.19 |
| 316 L 1200 grit | 0.3 ± 0.06 | 2.32 ± 0.47 | 2.96 ± 0.03 |
| 316 L 4000 grit | 0.04 ± 0.01 | 0.35 ± 0.1 | 0.46 ± 0.1 |

TABLE 2

List of $Ca^{2+}$ and $HPO_4^{2-}$ concentrations, precipitation rate and composition of Ca-P coatings on cp.Ti and Ti6Al4V.

|  |  | TCS | HBSS |
|---|---|---|---|
| Concentration (mM) | $Ca^{2+}$ | 3.0 | 1.26 |
|  | $HPO_4^{2-}$ | 1.87 | 0.78 |
| Precipitation rate of coating | No Pre-Ca | 0.5 µm/hr | 1 µm/wk |
|  | Pre-Ca | 1 µm/hr | 3 µm/wk |
| Composition of coating |  | apatite, OCP | apatite |

Literature references

1. Y. Fujishiro, T. Sato and A. Okuwaki, "Coating of hydroxyapatite on metal plates using thermal dissociation of calcium—EDTA chelate in phosphate solutions under hydrothermal conditions", *J. Mater. Sc: Mater in Med,* 6, pp. 172–176, 1995

2. S. R. Radin and P. Ducheyne, *J. Biom. Mater. Res.,,* 27, pp. 35, 1993

3. T. Hanawa, "Titanium and its oxide film: a substrate for forming apatite", in Proc. of the Bone Biomaterial Interface Workshop, Toronto, December 1990, J. E. Davies ed., Univ. Toronto Press, pp. 49–61, 1991

4. E. Leitão, M. A. Barbosa and K. de Groot, "In vitro calcification of orthopaedic implant materials", *J. Mater. Sc: Mater in Med,* 6, pp. 849–852, 1995

5. P. Ducheyne, S. Radin and K. Ishikawa, "The rate of calcium phosphate precipitation on metal and ceramics, and the relationship to bioactivity", in Bone Bonding Biomaterials, P. Ducheyne, T. Kokubo & C. A. van Blitterswijk (eds), Reed Heathcare Communications, pp. 213–218, 1992

6. Li, P, PhD Thesis, Leiden University (1993)

What is claimed is:

1. An implantable device comprising a material having a precipitate enhancing roughened surface, before coating, with an average peak distance between 10 and 1,000 nm and having an average depth wherein the roughened surface is coated with a layer of a calcium phosphate precipitate provided in vitro wherein at least a portion of the layer has a thickness greater than the average depth of the roughened surface.

2. The implantable device according to claim 1 wherein the average peak distance is between about 20 nm and about 500 nm.

3. The implantable device according to claim 1 wherein the roughened surface, before coating, has an average depth between about 20 nm and about 2,000 nm.

4. The implantable device according to claim 1, wherein the layer of calcium phosphate precipitate has a thickness of about 50 nm to about 200 µm.

5. The implantable device according to claim 1, wherein said material is selected from the group consisting of a metal, a metal alloy, a ceramic material, a natural or synthetic polymer, and a composite of any of these materials.

6. A process for producing a calcium phosphate coated implantable device, comprising subjecting a porous or non-porous material to a surface treatment until a roughened surface with an average peak distance between about 10 and about 1,000 nm is obtained and in vitro coating the surface with a layer of a calcium phosphate.

7. The implantable device according to claim 1 wherein the calcium phosphate layer comprises an amorphous structure of small crystals.

8. The implantable device according to claim 1 wherein the calcium phosphate layer comprises calcium ions and phosphate ions and one or more ions selected from the group consisting of hydroxide, chloride, sulphate, and nitrate anions and hydrogen, sodium, potassium and magnesium cations.

9. The implantable device according to claim 1 wherein the calcium phosphate layer does not comprise hydroxyapatite.

10. The implantable device according to claim 5 wherein the metal is titanium or tantalum and the metal alloy is a titanium alloy.

11. The implantable device according to claim 1, wherein the layer of calcium phosphate precipitate has a thickness of about 1 µm to about 50 µm.

* * * * *